United States Patent [19]

Dixon

[11] Patent Number: 4,976,275
[45] Date of Patent: Dec. 11, 1990

[54] METHOD OF BREAKING A NAIL BITING HABIT

[76] Inventor: Kathy M. Dixon, 308 N. Clayton, Wynnewood, Okla. 73098

[21] Appl. No.: 365,724

[22] Filed: Jun. 14, 1989

[51] Int. Cl.$^5$ ............................. A61C 5/14; A61F 5/37
[52] U.S. Cl. ...................................... 128/860; 128/880
[58] Field of Search ................ 128/15, 859, 860, 861, 128/862, 848, 880

[56] References Cited

U.S. PATENT DOCUMENTS

| | | | |
|---|---|---|---|
| 735,762 | 8/1903 | Hare | 128/15 |
| 770,853 | 9/1904 | Hare | 128/15 |
| 1,010,147 | 11/1911 | Ivory | 128/15 |
| 1,354,652 | 10/1920 | Jefferies | 128/848 |
| 1,389,436 | 8/1921 | Cameron | 128/15 |
| 1,474,497 | 11/1923 | Stolper | 128/15 |
| 2,037,079 | 4/1936 | Locke | 128/859 |
| 2,077,245 | 4/1937 | Locke | 128/859 |
| 2,600,025 | 6/1952 | Sage | 128/860 |
| 2,695,622 | 11/1954 | Herod | 128/848 |
| 3,219,033 | 11/1965 | Wallshein | 128/860 |
| 3,277,892 | 10/1966 | Tepper | 128/860 |
| 3,522,805 | 8/1970 | Wallshein | 128/860 |
| 3,734,084 | 5/1973 | Ousterhout | 128/15 |
| 3,867,927 | 2/1975 | Hergott | 128/15 |
| 4,002,162 | 1/1977 | Weisser | 128/15 |
| 4,471,771 | 9/1984 | Steven | 128/859 |

*Primary Examiner*—Robert A. Hafer
*Assistant Examiner*—Michael Brown
*Attorney, Agent, or Firm*—T. M. Gernstein

[57] ABSTRACT

A method for breaking a nail biting habit includes preventing a patient from moving his tongue into a position to contact the fingernail or fingertip when such fingernail or fingertip is placed in the patient's mouth for the purpose of biting the fingernail.

1 Claim, 2 Drawing Sheets

METHOD OF BREAKING A NAIL BITING HABIT

TECHNICAL FIELD OF THE INVENTION

The present invention relates to the general art of medicine, and to the particular field of habit breaking, specifically, the field of breaking oral habits.

Nail biting, or onychophagia, is a nervous affliction or neurosis in which the free edge of the fingernails is bitten. Nail biting is most often associated with early adolescence and childhood, and is generally outgrown or simply stopped when the child reaches a certain age.

However, there are known cases of onychophagia that continue beyond adolescence. If such a habit continues much beyond early adolescence, it can create several health problems, such as tense neck muscles, headaches, and even dislocation of the jaw (TMJ syndrome). Thus, if unchecked, the otherwise innocuous habit of nail biting can become a serious health problem.

While the art contains several means for breaking a nail biting habit, such as coatings and coverings for the fingernails, and the like, none of these devices has been entirely satisfactory or effective in preventing the serious problem of nail biting which continues into adulthood.

The inventor has observed that the serious problem of nail biting involves the gratification received by the patient when his tongue contacts the nail or the fingertip during the nail biting process. It is for this reason that the above-mentioned solutions have not been successful—they do not prevent the just-mentioned gratification that is received via the patient's tongue.

While there are many devices known in the art for controlling the tongue, such as during various oral and dental surgical procedures, for preventing tongue thrusting or for correcting speech problems, such devices are for specific purposes that are unrelated to curing a nail biting problem.

In fact, the inventor is not aware of any literature that suggests that there is a connection between serious nail biting and the gratification received via the tongue. More specifically, the inventor is not aware of any device or method that is intended to prevent nail biting by controlling the tongue. Since this habit is generally passed off as simply a manifestation of adolescence, and is generally considered to be innocuous and outgrowable, the art has a deficiency in the area of curing a serious nail biting habit of an adult. This adult is either left to use the simple devices and methods used on children, or is left to suffer serious problems, such as those mentioned above.

Accordingly, there is a need in the art for a method of curing a serious, adult, nail biting habit.

OBJECTS OF THE INVENTION

It is a main object of the present invention to provide a method of curing a serious problem of nail biting.

It is another object of the present invention to provide a method of curing serious problem of nail biting using the concept that such problem is associated with the gratification received from the habit via the tongue.

It is another object of the present invention to provide a method of curing a serious problem of nail biting by preventing a patient's tongue from contacting the fingernails and/or fingertips placed in his mouth for a nail biting process.

SUMMARY OF THE INVENTION

These, and other, objects are achieved by preventing the tongue of a patient from contacting his fingernails and/or fingertips that are placed in his mouth in position to be bitten.

The present inventor has observed that the tongue is the vehicle through which a nail biter receives gratification. The inventor has also observed that during a nail biting process, the tongue seeks out rough areas of the nail and guides the teeth to the exact location to begin biting.

Since neither nails nor teeth, per se, have feeling, without the tongue, the patient will not receive any pleasure from nail biting. Thus, the inventor has observed that the serious problem of nail biting is really a habit of the tongue.

Thus, the method of the present invention breaks the habit of serious nail biting by preventing the patient's tongue from reaching a nail or fingertip that has been placed between the teeth for the purposes of biting. By preventing the tongue from being able to touch and rub against the fingers or the nails, gratification is prevented, and the habit will eventually be broken.

In one embodiment of the method, a shield is affixed to the patient's teeth in a position which prevents that patient's tongue from reaching a position to touch nails and/or fingers that have been placed in the mouth for the purpose of nail biting. The device will not hinder normal chewing, talking, oar breathing, and will not be normally visible. However, the device will achieve the above-mentioned results.

While the implantation of a device which inhibits tongue movement is a drastic step, the serious consequences of compulsive nail biting in an adult, as mentioned above, may require such Draconian action.

DESCRIPTION OF THE DRAWING FIGURES

DETAILED DESCRIPTION OF THE PREFERRED EMBODIMENT OF THE INVENTION

As discussed above, the serious problem of nail biting is really a tongue-related problem, in that the habit is perpetuated due to the gratification that is received via the patient's tongue contacting the nails and/or the fingertips as they are being bitten. Accordingly, the method embodying the present invention seeks to cure this habit by preventing such gratification.

The method thus includes the step of mounting some sort of shield in the patient's mouth in a position to prevent the tongue from reaching a position in which it can contact either the fingertips or the nails of that patient when such fingertips or nails are inserted into the patient's mouth for the purpose of nail biting. However, the method further includes locating this shield so that other, normal, oral operations, such as eating, talking, and the like, can be carried out without undue interference from the shield.

The shield is thus most effectively placed in the frontal area of the mouth so that the tongue can move freely behind the shield, but cannot move over it to reach the incisor area of the mouth. In severe cases, the shield will be permanently affixed to the patient's teeth until such time as the habit is broken. As mentioned above, this serious measure may be necessary in extreme cases, while other cases can be cured using a shield that is releasably connected to the patient's teeth in the manner of a dental retainer.

Figure 1:
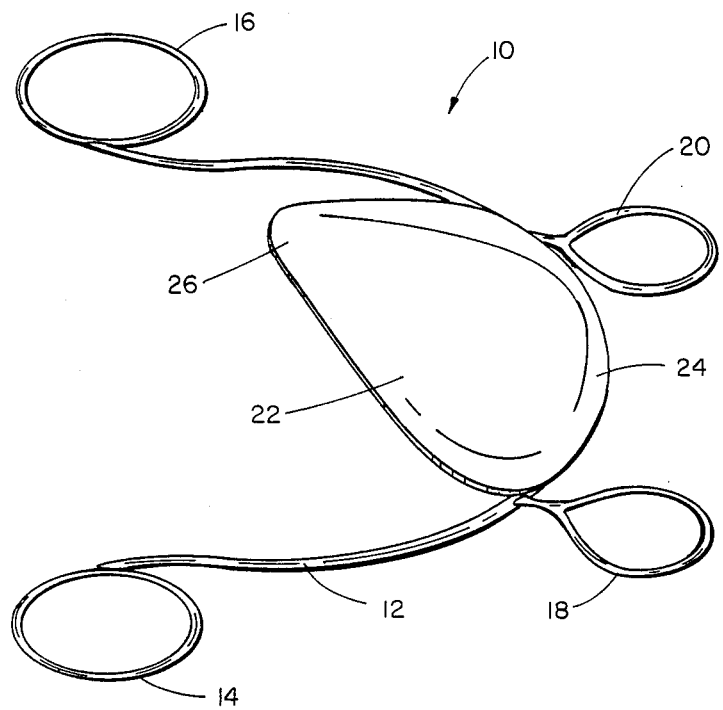
FIG. 1 is a perspective view of a device that can be used to carry out the method of the present invention.
Figure 3:
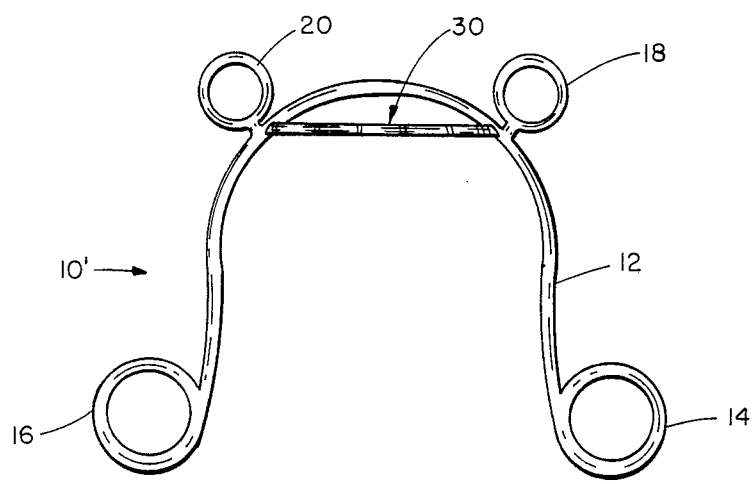
FIG. 3 is a top plan view of another device that can be used to carry out the method of the present invention.
Figure 4:
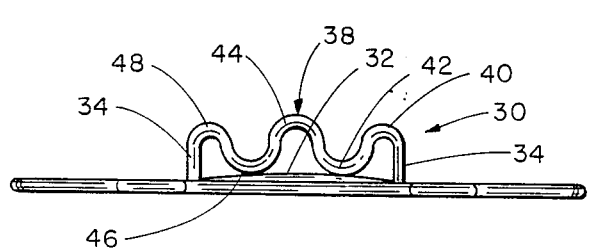
FIG. 4 is a front elevational view of the device shown in FIG. 3.
Figure 2:
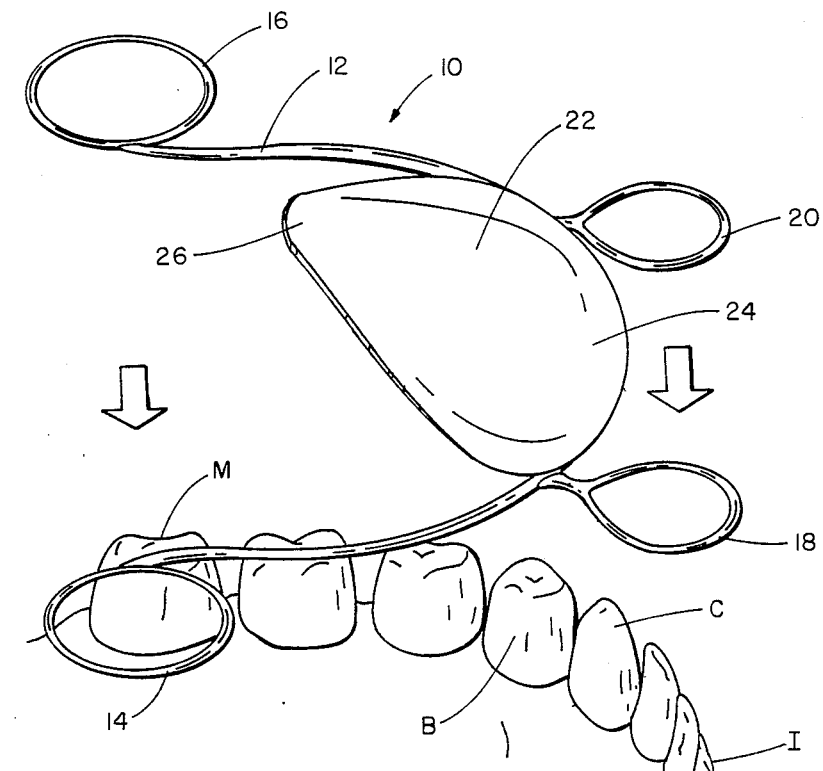
FIG. 2 is a perspective view of the FIG. 1 device being placed onto a patient's teeth in order to carry out the method of the present invention.
Figure 5:
FIG. 5 is a rear elevational view of the device shown in FIG. 3.
Figure 5:

One example of a shield that is suitable for carrying out the above-discussed method is shown in FIGS. 1 and 2. It is noted that the method can be carried out using other devices, and the device shown in the figures are merely examples, and are not intended as a limitation. The exact device and its method of attachment will be left to the patient and the medical professional in charge of the procedure.

Thus, as shown in FIGS. 1 and 2, a unitary shield assembly 10 includes a base 12 having tooth-engaging anchor loops 14-20 thereon and located in position to be affixed to the patient's teeth. For example, loops 14 and 16 can be positioned to engage the patient's molars M; whereas loops 18 and 20 can be positioned to engage the patient's bicuspids B, cuspids C or incisors I. The loops can be designed to be releasably engaged with such teeth or can be designed to be affixed, as by gluing or the like, to such teeth.

The assembly 10 further includes a shield 22 mounted at a proximal end 24 thereof to the base 12 near loops 18 and 20, and which extends to a distal end 26 that is spaced from such base and loops. The shield 22 tapers from the proximal end to the distal end to define a rounded edge at that distal end. The rounded edge can be located on either side of the lateral centerline of the patient's mouth, such as the side shown in FIG. 1, or can be located directly in the middle of the mouth. The side placement is preferred however for various reasons, such as comfort or the like.

Figure 6:
FIG. 6 is a side elevational view of the device shown in FIG. 3.

A further shield assembly 10' that can be used to carry out the method of the present invention is shown in FIGS. 3-6 and is shown as including a base 12 having loops 14-20 similar to such elements in assembly 10, and having a shield 30 that extends above the plane containing the base and loops. The shield 30 extends across the base between the loops 18 and 20, and includes a cross beam 32 having its ends attached to the base 12, and an upstanding end element 34 on each end thereof. A body 38 extends above the cross beam and between the end element and includes a plurality of reverse curves 40-48. As best shown in FIG. 6, the shield is angled with respect to the plane containing the base 12, and extends inwardly of the patient's mouth.

It is understood that while certain forms of the present invention have been illustrated and described herein, it is not to be limited to the specific forms or arrangements of parts described and shown.

I claim:

1. A method of breaking a severe adult nail biting habit comprising:
   (A) placing a tongue shield assembly in a patient's mouth on the patient's lower jaw, the patient's mouth including a frontal portion, a rear portion, incisor and bicuspid teeth located in the frontal portion and molars located in the rear portion, with the patient's throat being located adjacent to the rear portion of the mouth;
   (B) positioning the tongue shield in the frontal portion of the patient's mouth and covering the frontal portion of the patient's mouth from the incisor teeth therein to the bicuspid teeth therein;
   (C) orienting the tongue shield to extend essentially parallel to a plane containing the cutting edges of said bicuspid and incisor teeth with a front portion of said tongue shield located adjacent to the frontal portion of the patient's mouth and a rear portion thereof located adjacent to the rear portion of the patient's mouth;
   (D) permitting free movement of the patient's tongue behind the rear portion of the tongue shield and free movement of items, such as food, into the patient's mouth; and
   (E) preventing movement of the patient's tongue into the frontal area of the patient's mouth by means of said tongue shield so a tip of that tongue cannot contact a nail or a fingertip that has been inserted into the patient's mouth for the purpose of nail biting; and
   (F) gluing the tongue shield to the patient's molars.

* * * * *